(12) United States Patent
Chelly

(10) Patent No.: US 6,485,475 B1
(45) Date of Patent: Nov. 26, 2002

(54) INTRODUCER NEEDLE FOR CONTINUOUS PERINEURAL CATHETER PLACEMENT

(75) Inventor: Jacques E. Chelly, Houston, TX (US)

(73) Assignee: The Board of Regents of the University Texas System, Austin, TX (US)

( * ) Notice: Subject to any disclaimer, the term of this patent is extended or adjusted under 35 U.S.C. 154(b) by 0 days.

(21) Appl. No.: 09/516,980

(22) Filed: Mar. 1, 2000

(51) Int. Cl.[7] .............................................. A61M 25/00
(52) U.S. Cl. .................. 604/264; 604/272; 604/164.01; 604/164.13; 604/164.09
(58) Field of Search ............................. 604/264, 164.13

(56) References Cited

U.S. PATENT DOCUMENTS

| | | | | |
|---|---|---|---|---|
| 3,782,381 A | * | 1/1974 | Winnie ..................... | 128/214.4 |
| 4,958,901 A | * | 9/1990 | Coombs ....................... | 604/44 |
| 5,215,105 A | * | 6/1993 | Kizelshteyn et al. ........ | 604/264 |
| 5,215,527 A | * | 6/1993 | Beck et al. .................. | 604/164 |
| 5,215,528 A | * | 6/1993 | Purdy et al. ................. | 604/164 |
| 5,267,971 A | * | 12/1993 | Brimhall ..................... | 604/177 |
| 5,304,141 A | * | 4/1994 | Johnson et al. ............. | 604/158 |
| 5,693,030 A | * | 12/1997 | Lee et al. .................... | 604/117 |
| 5,897,533 A | * | 4/1999 | Glickman .................... | 604/256 |

OTHER PUBLICATIONS

Peripheral Nerve Blocks A Color Atlas, Jacques E. Chelly, Editor, 1999.

* cited by examiner

Primary Examiner—Ira S. Lazarus
Assistant Examiner—Tu Cam Nguyen
(74) Attorney, Agent, or Firm—Duane Morris LLP

(57) ABSTRACT

The present invention is directed toward an improved catheter introducer needle capable of introducing a catheter into a body at a deflection angle in the range of 40–75° from the axis of the needle. This invention provides for a continuous perineural placement of a catheter. The present invention is also directed toward an introducer needle/catheter system comprising the needle of the present invention and a catheter extending through the needle such that it extends out beyond the tip of the needle at an angle of deflection in the range of 30–75° from the axis defined by the catheter within the main channel of the needle. This invention is useful in delivering pharmacological agents, such as local anesthetics, to nerves in various regions of the body including, but not limited to, the arms and shoulders.

20 Claims, 2 Drawing Sheets

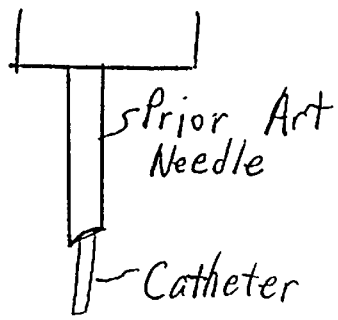
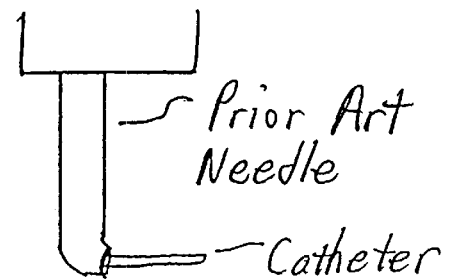
FIG 1A
FIG 1B
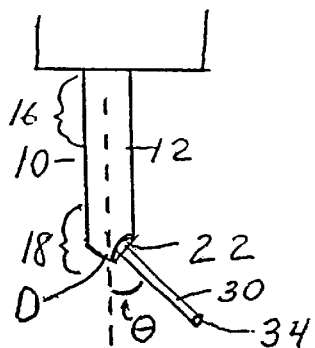
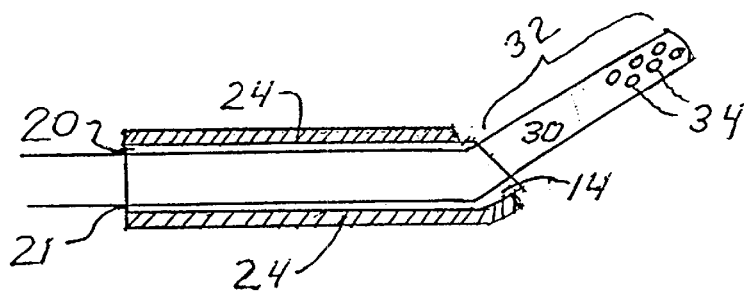
FIG 2A
FIG 2B

INTRODUCER NEEDLE FOR CONTINUOUS PERINEURAL CATHETER PLACEMENT

BACKGROUND OF THE INVENTION

1. Field of the Invention

The present invention is directed toward an improved catheter introducer needle for continuous perineural infusion allowing the introduction of a catheter into a body at a deflection angle in the range of 30–75° from the axis of the needle. This invention provides for a continuous perineural placement of a catheter. The present invention is also directed toward an introducer needle/catheter system comprising the needle of the present invention and a catheter extending through the needle such that it extends out beyond the tip of the needle at an angle of deflection in the range of 30–75° from the axis defined by the catheter within the main channel of the needle. This invention is useful in delivering pharmacological agents, such as local anesthetics, to nerves in various regions of the body including, but not limited to, the neck, arms, shoulders, back, thigh and legs.

2. Description of the Prior Art

Needles are used in the prior art to place catheters into the body. Prior art introducer needles allow a catheter to be displaced at an angle of either 0° or 90° to the longitudinal axis of the needle, as shown in FIGS. 1A and 1B, respectively. The 90° displacement is achieved with prior art needles, such as the tuhoy needle, used for epidural applications.

The angular displacement of catheters which are implanted using prior art introducer needles are greatly inappropriate in view of the common geometric relationships between the tip of the introducer needle and the position of various nerves within the body of a patient. The term "patient," as used herein, encompasses human beings and animals. Very few nerves within a patient's body are displaced parallel or perpendicular to the surface of the body. It is ideal for the portion of the catheter which extends beyond the introducer needle to be in substantially parallel alignment with the nerve which one desires to treat by injection of drugs through the catheter. The closer the catheter is aligned with the nerve, the greater is the efficiency of drug delivery through the catheter to treat the nerve. For most nerves in the body which are not displaced parallel or perpendicular to the surface of the body, prior art introducer needles do not position a catheter in closer alignment with those nerves, as shown in FIG. 3A.

Many drugs which are delivered for anesthesia purposes are toxic. The inefficiency of prior art introducer needles results in increased probability of patient toxicity poisoning resulting from the dispersion of drugs which are not delivered directly to the nerve to be treated.

SUMMARY OF THE INVENTION

The present invention is directed to an improved catheter introducer needle which is capable of more closely aligning a catheter with a nerve inside a body than prior art introducer needles. The needle of the present invention results in increased efficiency of drug delivery to a nerve, thereby reducing the volume of drugs which must be delivered. This reduction in drug dosage reduces the probability of patient toxicity poisoning. The present invention is particularly well suited to home health care applications where reducing the volume of toxic drugs delivered to the patient is highly desirable.

The introducer needle of the present invention comprises a tubular body comprising an exterior surface, an interior surface, a first end region, and a second end region. The introducer needle further comprises a channel extending the length of the body to define a channel axis and a first opening located in the first end region contiguous with the channel. The introducer needle may be connected to a tubing.

The introducer needle further comprises a second opening located in the second end region of the body contiguous with the channel. The second opening is positioned such that a flexible catheter extending through the channel and the second opening is deflected at an angle in the range of 30–75° from the channel axis.

The present invention is also directed toward an introducer needle/catheter system comprising an introducer needle as described above and further comprising a flexible catheter extending through the channel, first opening and second opening of the body such that the portion of the catheter that extends beyond the second opening is displaced at an angle in the range of 30–75° with respect to the portion of the catheter in the channel.

DESCRIPTION OF THE PREFERRED EMBODIMENTS

Figure 3A:
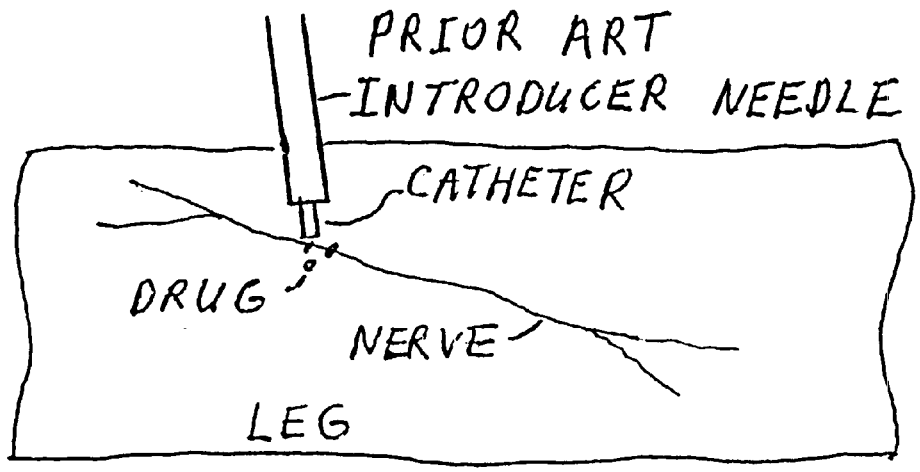
FIG. 3A is a side view of a first embodiment of a prior art introducer needle/catheter system inserted in a patient.
Figure 3B:
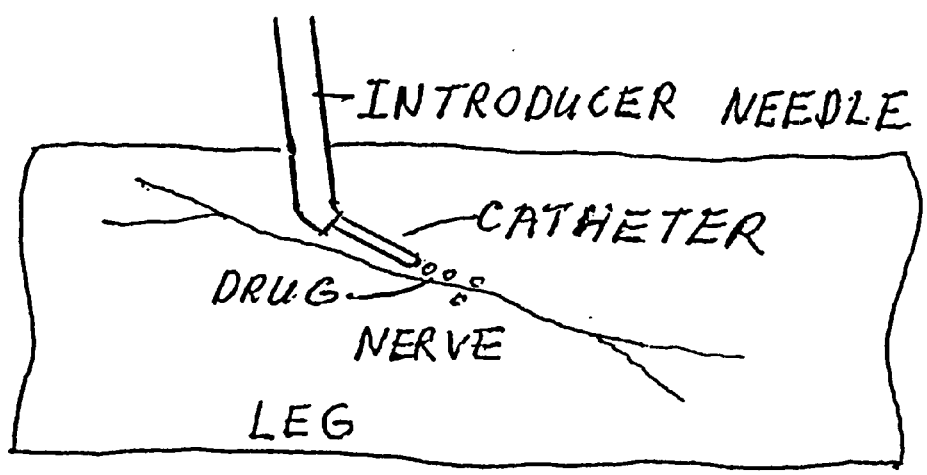
FIG. 3B is a side view of a first embodiment of the introducer needle/catheter system of the present invention inserted in a patient.
Figure 1A:
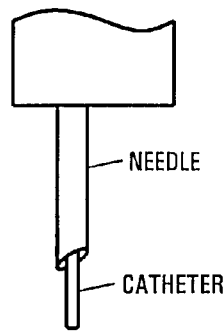
FIG. 1A is a side view of a first embodiment of a prior art introducer needle.
Figure 1B:
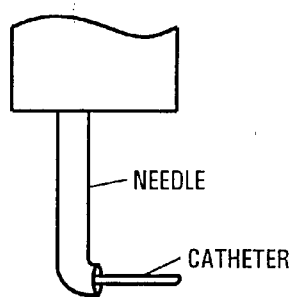
FIG. 1B is a side view of a second embodiment of a prior art introducer needle.
Figure 2A:
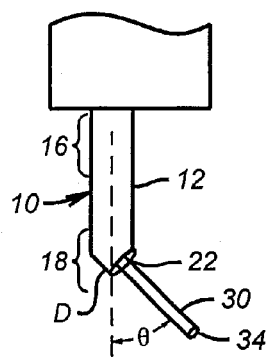
FIG. 2A is a side view of a first embodiment of the introducer needle/catheter system of the present invention.
Figure 2B:
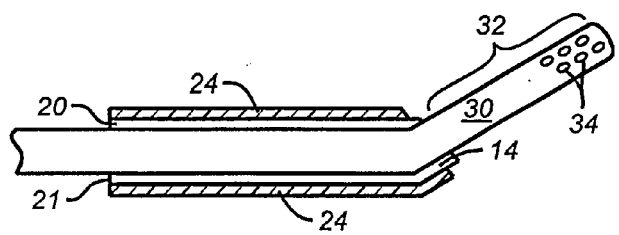
FIG. 2B is a side cutaway view of a second embodiment of the introducer needle/catheter system of the present invention.
Figure 3A:
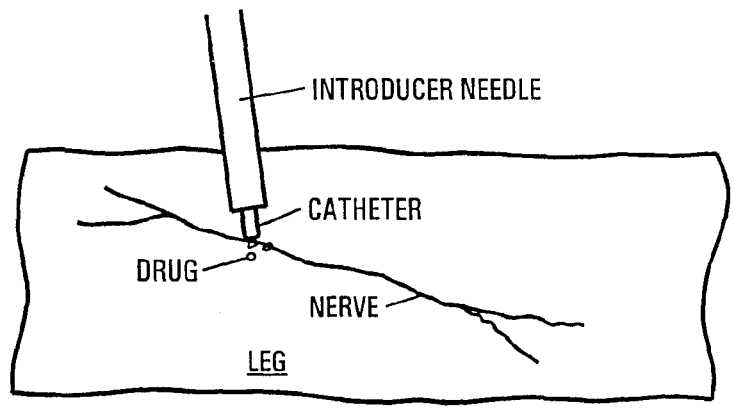
Figure 3B:
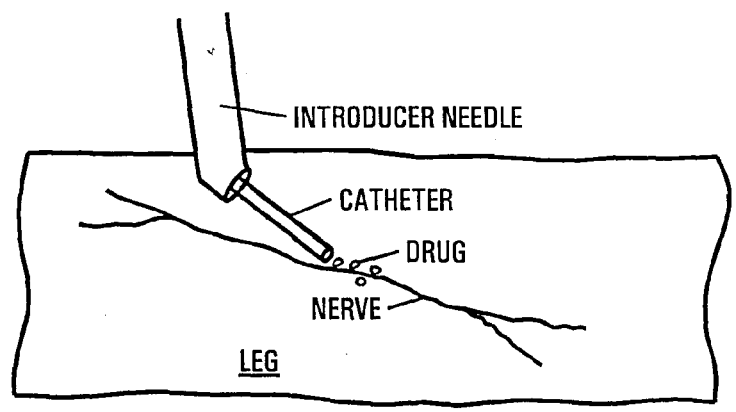

As shown in FIGS. 2A–2B, the introducer needle of the present invention comprises a tubular body 10 comprising an exterior surface 12, an interior surface 14, a first end region 16, and a second end region 18. In one preferred embodiment, the needle has a gauge in the range of 14–20. The optimum gauge will be a function of several factors including, but not limited to, the location in the body of the patient where the needle is to be injected, the physical size of the patient, and the nerve to be treated. In another preferred embodiment, the body has a gauge in the range of 18–19.

In a preferred embodiment, the needle body has a length in the range of 0.5–1.0 inches. The optimum length of the needle body will be a function of the location in the body of the patient where the needle is to be injected, the physical size of the patient, and the nerve to be treated.

The introducer needle further comprises a channel 20 extending the length of the body to define a channel axis and a first opening 21 located in the first end region contiguous with the channel, as shown in FIG. 2B. The channel axis is denoted by the vertical dotted line in FIG. 2A.

In some applications, electrical current is administered to a nerve within the patient's body. This current may be administered in conjunction with the delivery of drugs through a catheter. In such arrangements, the introducer needle is electrically insulated.

In a preferred embodiment, the invention further comprises electrical insulation 24 placed upon the exterior surface of the body, as shown in FIG. 2B. In another preferred embodiment, the electrical insulation covers the exterior surface of the body, as shown in FIG. 2B. In a preferred embodiment, the electrical insulation is made from a biocompatible plastic material. The desirability of electrical insulation, as well as the optimum length of the needle, is a function of the location where treatment is to be administered. Examples of preferred needle lengths and uses of insulated and noninsulated needles are summarized in the table below:

| Approaches | Length (inches) | Insulated | Noninsulated |
| --- | --- | --- | --- |
| interscalene | 1–2 | yes | yes |
| femoral | 2–4 | yes | no |
| fascia iliacus | 2–4 | no | yes |
| posterior sciatic | 4–6 | yes | no |
| lateral sciatic | 2–6 | yes | no |
| anterior sciatic | 4–6 | yes | no |
| posterior popliteal fossa | 4–6 | yes | no |
| lateral popliteal fossa | 4–6 | yes | no |
| lumbar plexus | 4–6 | yes | no |
| supraclavicular | 2–6 | yes | yes |
| infraclavicular | 2–6 | yes | no |
| axillary | 1–4 | yes | yes |

The introducer needle further comprises a second opening 22 located in the second end region of the body contiguous with the channel, as shown in FIG. 2B. The, second opening is positioned such that a flexible catheter 30 extending through the channel and the second opening is deflected by a portion of the tubular body at an angle in the range of 30–75° from the channel axis as shown in FIG. 2B. As shown in FIG. 2B, this deflection occurs at the location of the second opening.

The present invention is also directed toward an introducer needle/catheter system. This embodiment of the invention comprises an introducer needle, as described above, as well as a flexible catheter 30 extending through the channel, first opening, and second opening of the tubular body, such that the portion of the catheter that extends beyond the second opening is displaced at an angle in the range of 30–75° with respect to the portion of the catheter in the channel, as shown in FIGS. 2A and 2B. The portion of the catheter in the channel extends along the channel axis defined by the channel, as shown in FIG. 2B.

In a preferred embodiment, the catheter comprises an extension region 32 extending out of the needle body beyond the second opening, as shown in FIG. 2B. In one preferred embodiment, the extension region comprises a tip comprising an opening 34 as shown in FIG. 2A. In another preferred embodiment, the extension region comprises a multiplicity of openings 34, as shown in FIG. 2B. Drugs flow out of the catheter through the openings in the catheter.

The angle of catheter deflection is illustrated by the angle θ in FIG. 2A. The second opening may be located, entirely or partially, in the side of the needle body. The magnitude of the angular deflection is a function of the angle and length of the deflection segment of the second end region of the needle body, denoted by the label "D" in FIG. 2A. Angular deflection may also be achieved by the use of an elbow geometry in the second end region of the tubular body. The use of an elbow having an angular deflection in the range of 30–75° will allow one to achieve an angular deflection of a catheter in the range of 30–75°.

The foregoing disclosure and description of the invention are illustrative and explanatory. Various changes in the size, shape, and materials, as well as in the details of the illustrative embodiments may be made without departing from the spirit of the invention.

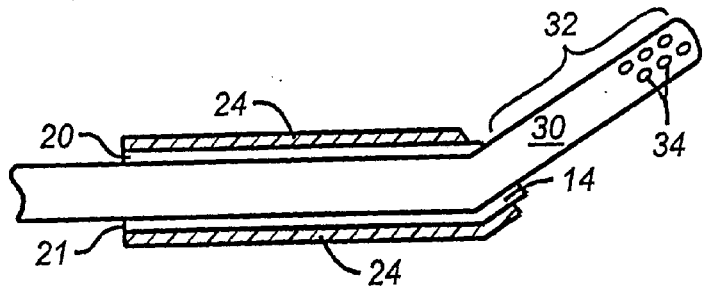

What is claimed is:

1. An introducer needle capable of introducing a catheter comprising:
   a. a tubular body comprising an exterior surface, an interior surface, a first end region, and a second end region;
   b. a channel extending the length of said body to define a channel axis;
   c. a first opening located in said first end region contiguous with said channel; and
   d. a second opening located in said second end region contiguous with said channel and positioned such that a flexible catheter extending through said channel and second opening is deflected by a portion of the tubular body at an angle in the range of 30–75 degrees from the channel axis.

2. The needle needle of claim 1, further comprising electrical insulation placed upon the exterior surface of said body.

3. The needle of claim 1, wherein said insulation covers the exterior surface of said body.

4. The needle of claim 1, wherein said body has a length in the range of 0.5–10.0 inches.

5. The needle of claim 1, wherein said body has a gauge in the range of 14–20.

6. The needle of claim 5, wherein said body has a gauge in the range of 18–19.

7. The needle of claim 1 further comprising a flexible catheter extending through said channel, said first opening and said second opening such that the portion of said catheter that extends beyond said second opening is displaced at an angle in the range of 30–75 degrees with respect to the portion of said catheter in said channel.

8. The needle of claim 7, wherein said body has a length in the range of 0.5–10.0 inches.

9. The needle of claim 7, wherein said body has a gauge in the range of 14–20.

10. The needle of claim 2 further comprising a flexible catheter extending through said channel, said first opening and said second opening such that the portion of said catheter that extends beyond said second opening is displaced at an angle in the range of 30–75 degrees with respect to the portion of said catheter in said channel.

11. The needle of claim 10, wherein said body has a length in the range of 0.5–10.0 inches.

12. The needle of claim 10, wherein said body has a gauge in the range of 14–20.

13. An introducer needle/catheter system comprising:
   a. a tubular body comprising an exterior surface, an interior surface, a first end region, and a second end region;
   b. a channel extending the length of said body to define a channel axis;
   c. a first opening located in said first end region contiguous with said channel;
   d. a second opening located in said second end region contiguous with said channel and positioned such that a flexible catheter extending through said channel and second opening is deflected at an angle in the range of 30–75 degrees from the channel axis; and e. a flexible catheter extending through said channel, said first opening and said second opening such that the portion of said catheter that extends beyond said second opening is displaced at an angle in the range of 30–75 degrees with respect to the portion of said catheter in said channel at the location of the second opening.

14. The system of claim 13 wherein said catheter comprises an extension region extending out of said body beyond said second opening.

15. The system of claim 14 wherein said extension region comprises a tip comprising an opening.

16. The system of claim 14 wherein said extension end region comprises a multiplicity of openings.

17. The system of claim 13, further comprising electrical insulation placed upon the exterior surface of said body.

18. The system of claim 13 wherein said body has a gauge in the range of 14–20 and a length in the range of 0.5–10.0 inches.

19. An introducer needle capable of introducing a catheter comprising:

a. a tubular body comprising an exterior surface, an interior surface, a first end region, and a second end region, said body having a length in the range of 0.5–10.0 inches and a gauge in the range of 14–20;

b. a channel extending the length of said body to define a channel axis;

c. a first opening located in said first end region contiguous with said channel; and c. a second opening located in said second end region contiguous with said channel and positioned such that a flexible catheter extending through said channel and second opening is deflected by a portion of the tubular body at an angle in the range of 30–75 degrees from the channel axis.

20. The needle needle of claim 19, further comprising electrical insulation placed upon the exterior surface of said body.

* * * * *

UNITED STATES PATENT AND TRADEMARK OFFICE
CERTIFICATE OF CORRECTION

PATENT NO.    : 6,485,475 B1
DATED         : November 26, 2002
INVENTOR(S)   : Chelly It is certified that error appears in the above-identified patent and that said Letters Patent is hereby corrected as shown below:

Title page, showing the illustrative figure should be deleted to be replaced with the attached title page.

Item [57], ABSTRACT,
Line 3, please delete "40" and insert -- 30 --.

Drawings,
Sheets 1-2, consisting of Figs. 1A, 1B, 2A, 2B, 3a and 3b, should be replaced with the corrected drawing sheets 1-2, consisting of Figs. 1A, 1B, 2A, 2B, 3a and 3b, as shown on the attached pages.

Signed and Sealed this

Twenty-third Day of September, 2003

JAMES E. ROGAN
*Director of the United States Patent and Trademark Office*

(12) United States Patent
Chelly

(10) Patent No.: US 6,485,475 B1
(45) Date of Patent: Nov. 26, 2002

(54) INTRODUCER NEEDLE FOR CONTINUOUS PERINEURAL CATHETER PLACEMENT

(75) Inventor: Jacques E. Chelly, Houston, TX (US)

(73) Assignee: The Board of Regents of the University Texas System, Austin, TX (US)

( * ) Notice: Subject to any disclaimer, the term of this patent is extended or adjusted under 35 U.S.C. 154(b) by 0 days.

(21) Appl. No.: 09/516,980

(22) Filed: Mar. 1, 2000

(51) Int. Cl.[7] .............................................. A61M 25/00
(52) U.S. Cl. .................. 604/264; 604/272; 604/164.01; 604/164.13; 604/164.09
(58) Field of Search ............................ 604/264, 164.13

(56) References Cited

U.S. PATENT DOCUMENTS

| | | | | |
|---|---|---|---|---|
| 3,782,381 A | * | 1/1974 | Winnie | 128/214.4 |
| 4,958,901 A | * | 9/1990 | Coombs | 604/44 |
| 5,215,105 A | * | 6/1993 | Kizelshteyn et al. | 604/264 |
| 5,215,527 A | * | 6/1993 | Beck et al. | 604/164 |
| 5,215,528 A | * | 6/1993 | Purdy et al. | 604/164 |
| 5,267,971 A | * | 12/1993 | Brimhall | 604/177 |
| 5,304,141 A | * | 4/1994 | Johnson et al. | 604/158 |
| 5,693,030 A | * | 12/1997 | Lee et al. | 604/117 |
| 5,897,533 A | * | 4/1999 | Glickman | 604/256 |

OTHER PUBLICATIONS

Peripheral Nerve Blocks A Color Atlas, Jacques E. Chelly, Editor, 1999.

* cited by examiner

*Primary Examiner*—Ira S. Lazarus
*Assistant Examiner*—Tu Cam Nguyen
(74) *Attorney, Agent, or Firm*—Duane Morris LLP

(57) ABSTRACT

The present invention is directed toward an improved catheter introducer needle capable of introducing a catheter into a body at a deflection angle in the range of 40–75° from the axis of the needle. This invention provides for a continuous perineural placement of a catheter. The present invention is also directed toward an introducer needle/catheter system comprising the needle of the present invention and a catheter extending through the needle such that it extends out beyond the tip of the needle at an angle of deflection in the range of 30–75° from the axis defined by the catheter within the main channel of the needle. This invention is useful in delivering pharmacological agents, such as local anesthetics, to nerves in various regions of the body including, but not limited to, the arms and shoulders.

20 Claims, 2 Drawing Sheets